United States Patent [19]

Tedeschi

[11] 4,334,091
[45] Jun. 8, 1982

[54] PROCESS FOR PREPARING HALOVINYL CYCLOPROPANE CARBOXYLIC ACID SALTS

[75] Inventor: Robert J. Tedeschi, Whitehouse Station, N.J.

[73] Assignee: Air Products and Chemicals, Inc., Allentown, Pa.

[21] Appl. No.: 933,330

[22] Filed: Aug. 14, 1978

[51] Int. Cl.$^3$ ............................................. C07C 51/487
[52] U.S. Cl. ...................................... 562/506; 560/124; 560/192; 562/485; 562/486; 562/500; 562/488
[58] Field of Search .................... 560/124; 260/514 H; 562/506, 488, 480, 482, 486, 500

[56] References Cited

FOREIGN PATENT DOCUMENTS 2606635 8/1977 Fed. Rep. of Germany ...... 560/124

*Primary Examiner*—Michael L. Shippen
*Attorney, Agent, or Firm*—Douglas G. Glantz; E. Eugene Innis; James C. Simmons

[57] ABSTRACT

This invention relates to new compositions particularly suited for producing insecticidal intermediates. These compositions are mono basic salts of halovinyl cyclopropane derivatives particularly mono basic salts of dichlorovinyl chrysanthemic

6 Claims, No Drawings

PROCESS FOR PREPARING HALOVINYL CYCLOPROPANE CARBOXYLIC ACID SALTS

BACKGROUND OF THE INVENTION

1. Field of the Invention

This invention relates to compositions having a utility as pyrethroid insecticides or as intermediates for the preparation of pyrethroid insecticide esters, ethers, etc.

2. Description of the Prior Art

There are a multitude of patents and literature references relating to the preparation of synthetic pyethrines containing the cyclopropane ring system and the use of these compounds as insecticidal intermediates. These classes of insecticides have found wide acceptance because of their relative non-toxicity to mammals and their environmental compatability due to lack of persistence.

Various esters and ether derivatives of the pyrethrine class are shown in U.S. Pat. Nos. 3,979,519; 3,973,036; 3,981,903; 3,954,814; 3,927,068; 3,988,380; 4,003,945 and 4,000,181.

One of the previous methods for synthesizing the cyclopropane derivatives is known as the Staudinger process. It involves the reaction of ethyldiazoacetate and dimethylhexadiene to form the resulting carboxylate ester.

The halovinyl class of pyrethrines, which are more potent than the nonhalogen substituted compounds, can be also formed by the Staudinger process. This class is made by reacting ethyldiazoacetate with a compound such as 1,1-dichloro-4-methyl-1,3-pentadiene and then saponifying the resulting ester. The problems with the Staudinger process are: the diazoester is unstable (often explosive) and the diazo ester is suspected of being carcinogenic, thus making it a difficult process to handle on a large scale.

Recently, an improved process for preparing halosubstituted vinylcyclopropane carboxylates has been disclosed in Belgian Patent 833,278. In that patent, prenyl alcohol is condensed with an ortho ester, namely ethyl orthoacetate to form a gamma unsaturated carboxylate. The carboxylate then is reacted with a polyhalomethane, e.g. carbon tetrachloride to form a gamma-halo carboxylate which is followed by dehydrohalogenation and cyclization to bring about the formation of dihalovinyl cyclopropane carboxylate.

Another route based quite similarly to that disclosed in the Belgian patent comprises reacting an acetoacetic ester with ethanol to give the ethyl vinylether of an acetoacetic ester. Then the resulting ester is transetherified with prenyl alcohol to give an allyl vinyl ether of an acetoacetic ester, which thermally rearranges and decarboxylates to a gamma methylvinylketone. This ketone can then undergo polyhalomethane addition, and dehydrohalogenation and cyclization to give the product. One advantage of this process is that the ketone product can be oxidized in such a way to provide selectivity to the trans or cis isomer.

In a recent West German Offenlegungschrift, viz, 26 06 635, a process was disclosed relating to a method for producing dimethyl dichlorovinyl cyclopropane carboxylic acid derivatives. An exemplary acid derivative is prepared by reacting carbon tetrachloride with an olefin, i.e., dimethyl-propane-malonic acid diethyl ester followed by dehydrohalogenation, cyclization and hydrolysis to form the dichlorovinyl cyclopropane dicarboxylic acid (Ex. 3). In the Ex. 3 procedure hydrolysis of the ester to the diacid is effected by the addition of ice-cold hydrochloric acid.

SUMMARY OF THE INVENTION

This invention relates to compositions having insecticidal properties or compositions capable of preparing insecticidally active intermediates such as pyrethroid esters, ethers, etc.

Broadly the class of compositions are mono basic salts of cyclopropane derivatives represented by the formula

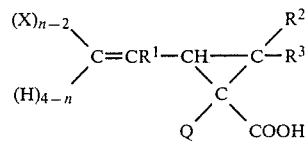

wherein:

X is a halogen atom selected from the group consisting of bromine and chlorine;

n is 3 or 4;

$R^1$ is hydrogen, a lower alkyl group having from 1 to 6 carbon atoms, cycloalkyl group, and an aryl group;

$R^2$ and $R^3$ are lower alkyl groups having from 1 to 6 carbon atoms, aryl groups, cycloalkyl and aralkyl;

Q is $CO_2M+$ where M is an alkali or alkaline earth metal.

The unique property of this particular class of compositions relates to its limited solubility in cold (5° to 10° C.) water. Because of its limited solubility the synthesis of an intermediate class of pyrethroid insecticides can be effected with simplicity since these compositions can be separated from the reaction medium and undesirable impurities in a simple, efficient manner. As a result of this unique property difficult extractive distillation or fractionation procedures can be minimized in order to effect product recovery. As a further embodiment, the monobasic acid salts can be decarboxylated to form the chrysanthemic acid derivative or reacted to form a host of different products.

DESCRIPTION OF THE PREFERRED EMBODIMENTS

The monobasic salts of this invention can be prepared in an efficient manner by following a relatively simple series of process steps. Essentially the first step involves reaction of a polyhalomethane with an olefinic dicarboxylic acid or ester to form a gamma halogen substituted compound of formula I.

FORMULA I

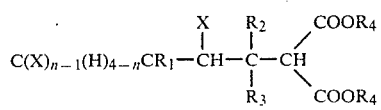

wherein:

n is 3 or 4;

$R_1$ is hydrogen, a lower alkyl group having from 1 to 6 carbon atoms, a cycloalkyl group and an aryl group; and $R_2$ and $R_3$ are lower alkyl groups having from 1 to 6 carbon atoms, aryl groups, and cycloalkyl and aralkyl groups.

The polyhalomethanes which can be reacted with the olefinic dicarboxylic acid ester have the formula $CX_nH_{4-n}$ wherein X is a halogen atom and n is 3 or 4. The halogen atom (X) can be fluorine, chlorine, bromine, and iodine, but where a fluorine atom is present, there must be a corresponding bromine, iodine or chlorine atom for each fluorine atom. Otherwise it would be impossible to effect dehydrohalogenation and formation of the vinyl linkage. When n is 3 the monohalovinyl substituted compound is produced, and where n is 4, the dihalovinyl compound is produced. For insecticidal purposes, the dihalovinyl compound is preferred, and accordingly, carbon tetrahalide is used as the reactant. Examples of polyhalomethanes which can be used in the addition reaction include chloroform, bromoform, iodoform, monofluorodibromomethane, monofluorodichloromethane, carbon tetrachloride, carbon tetrabromide, carbon tetraiodide, difluorodichloromethane, difluorodibromomethane, bromotrichloromethane and dibromodichloromethane. For reasons of efficiency and economy, carbon tetrabromide, carbon tetrachloride and bromotrichloromethane are the preferred reactants.

The olefinic dicarboxylic acid esters used in the process of this invention can be formed by effecting addition of a haloacetylic compound, e.g., chloromethyl butyne can have a variety of substituent groups thereon. In the formula $R_1$, preferably is hydrogen, although it can be lower alkyl ($C_{1-6}$) aryl, and cycloalkyl and aralkyl with 1–6 carbon atoms in the alkyl structures. Again, $R_2$ and $R_3$ can be substituted with alkyl groups ($C_{1-6}$), aryl, e.g., phenyl; cycloalkyl, and aralkyl, ($C_{1-6}$) in the alkyl portion. Examples of preferred olefinic compounds that can be used in the process include diethyl 1,1-dimethyl-2-propenylmalonate; dicyclohexyl 1,1-diphenyl-2-propenylmalonate; dimethyl 1,1-dicyclohexyl,-2-propenylmalonate; and 1,1-dimethyl,-2-propenylmalonate.

The general reaction of an olefinic dicarboxylic acid ester with a polyhalomethane is a known type reaction which proceeds by free radical addition ending in chain termination by the halomethane. Classes of conventional free radical initiators that can be used include ultraviolet light, electron beam, radical ions, peroxides, persulfates, transition metal salts, etc. Specific examples of free radical initiators include benzoyl peroxide, t-butyl perbenzoate, azo isobutyronitrile and ferric chloride.

In the reaction to produce the Formula I compound, the olefin reactant is generally dispersed in an excess of polyhalomethane rather than including a special solvent. However, a solvent, e.g., a hydrocarbon such as benzene or acetonitrile can be used in addition to the polyhalomethane. One of the advantages of using carbon tetrachloride and carbon tetrabromide as the solvent is that the olefin is soluble in the carbon tetrahalide reactant and the excess reactant increases the yield.

Essentially, the second step of this process involves the dehydrohalogenation and cyclization of the gamma halo substituted compound to form the compound represented by Formula II.

FORMULA II

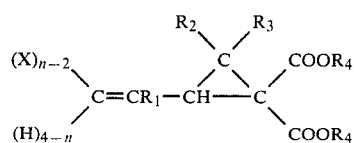

Generally, dehydrohalogenation and cyclization is simultaneously effected by reacting the gamma substituted compound with a base including, for example, sodium hydroxide, potassium hydroxide, potassium alkoxide in aprotic solvents such as methanol, ethanol, t-butanol, 2-ethoxyethanol including mixtures with water or aprotic solvents like diethylether, tetrahydrofuran, etc. Generally, the dehydrohalogenation and cyclization is effected over a temperature range of from 10° C. to 150° C., but preferably at about 40–75° C. because the compounds are slightly unstable at higher temperatures. Lower temperatures usually require longer reaction times.

The third step in the process, after dehydrohalogenation and cyclization, involves the conversion of the diacid salt to the monoacid salt. Since dehydrohalogenation and cyclization are carried out in the presence of an alkali metal hydroxide, the ester is saponified in situ to the diacid salt.

The isolation of the partial or monoacid salt of the halovinyl cyclopropane derivative and particularly the dichlorovinyl chrysanthemic acid salt is effected by acidifying the diacid salt dispersed in inert organic solvent, e.g., methanol, under carefully controlled conditions. The conditions employed, particularly where the dipotassium salt is being acidified is a careful acidification until the pH of the solution is roughly 3–7, preferably maintaining the temperatures at 0–10° C. The precipitate forms slowly, and the pH must be monitored carefully. The monosalt has limited solubility in cold 5–10° C. water and thus it precipitates at the pH of 3 to 7. The product precipitate thus obtained is largely free of unwanted residue (inorganic salts and impurities), and this principle procedure avoids the otherwise difficult extraction-distillation procedures with this unstable compound. If acidification is not carried out under controlled conditions and the pH of the system is not monitored, the diacid will form as indicated in West German Offenlegungsschrift 2,606,635 without forming the monoacid salt.

The following examples are provided to illustrate preferred embodiments of the invention but are not intended to restrict the scope thereof. All percentages are expressed as weight percentages.

Example 1-Polyhalomethane Addition ($CBrCl_3$)

A 39 gram sample of dimethyl 1,1-dimethyl-2-propenyl malonate was dissolved in an excess quantity (100 cc) of trichlorobromomethane. After 0.5 gms of benzoyl peroxide was added, the resulting solution was heated to reflux temperature. After refluxing for two hours, the reaction was terminated and the excess trichlorobromomethane removed by evaporation. The dimethyl (2-bromo-5,5,5-trichloro-1,1-dimethyl pentyl) malonate was recovered by crystallization in an ether/n-hexane medium. The melting point of the product was 61–63° C.

Example 2-Dehydrohalogenation and Cyclization

A 2.5 mmole portion of dimethyl (2-bromo-5,5,5-trichloro-1, 1-dimethyl pentenyl) malonate prepared in Example 1 was added to 5 ml ethanol and mixed in a reaction vessel. Then a liquid mixture comprising 115 mg sodium (5 mmoles) and 5 cc ethanol was added to the vessel and the temperature raised to 60° C. over a 20 minute period. The reaction medium was cooled, acidified with 5% aqueous HCl to a pH of about 3, and then diethylether was added in sufficient proportion (20 ml) to dissolve the dichlorovinyl cyclopropane diethylcarboxylate product formed. This ether mixture was water washed to remove soluble contaminants and then the ether solution was dried over magnesium sulphate. A crude dimethyl-2 (2,2,2-trichloroethyl)-3,3-dimethylcyclopropane dicarboxylate product was recovered by evaporating the ether.

Example 3-Product Purification Diester

A 406 gram portion (1.18 mole) of dicarboxylate product identical to that in Example 2 was added to a vessel. Then, 1.07 liters methanol were added to the vessel and heated to 45° C. for 30 minutes. Agitation of the mixture was maintained, and then a solution of 6 grams KOH (0.1 mole) in 382 cc methanol was added over a 40-minute period. Approximately one-half hour after the KOH solution was added to the reactor, 119 grams of powdered KOH (2 mole) was charged directly and the temperature then was raised to 65° C. After 1.5 hours reaction, the reaction was terminated and solvent was removed by vacuum stripping. The solid residue remaining in the reactor was dissolved in a minimum amount of water and the aqueous solution then extracted with ether.

A portion of the extract was cooled to 5° C. and the material slowly acidified with concentrated HCL. A white precipitate formed at a pH of about 4 and the precipitate removed by filtration. This precipitate was identified as the monopotassium salt of a dichlorovinyl chrysanthemic dicarboxylic acid.

This purification technique shows that by controlling the addition of acid and terminating where a mixed acid-acid salt are present, the product can be removed from the reaction mixture and obtained in high yield by a simple technique amenable to commercial practice.

When this last step was repeated and acidified with concentrated HCl to a pH of 2.0, a brown syrupy and tacky semisolid resulted. Impurities could be removed only by repeated dissolution and recrystallization with water and ether.

Example 4-Monopotassium Salt Preparation

The compound of Example 1 was treated with KOH in a 1:1 mole ratio at a temperature of 45° C. in the presence of methanol solvent to affect cyclization. The lower temperature (as compared to Example 2), results in reduced by product formation. After cyclization three additional moles of KOH were added and the mixture refluxed at about 70° C. for about 1.5 hours to form the dipotassium salt of a dichlorovinyl cyclopropane dimethyl carboxylate. Cyclization occurs when only one mole of KOH is used, whereas the three additional moles permit the formation of the dipotassium salt. An excess of KOH, e.g. 5-15%, often enhances completion of the reaction.

The resulting dipotassium salt then was stripped of methanol under vacuum and the solid residue remaining was dissolved in a minimum amount of water. Diethyl ether was then added to the aqueous solution, mixed and extracted to remove insoluble oils. The aqueous mixture then was treated with concentrated HCl at 5° C. under agitation to a pH of about 7 while precipitate is formed. Addition of acid was terminated at a pH of 4. The precipitate then was removed by filtration. The structure of the monopotassium salt of dichlorovinyl cyclopropane carboxylate was shown by various analytical techniques.

What is claimed:

1. A process for forming the compound having the formula

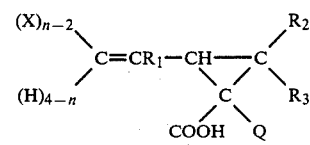

wherein:
X is a halogen atom selected from the group consisting of bromine and chlorine
n is 3 or 4;
$R^1$ is hydrogen or a lower alkyl group having from 1-6 carbon atoms, cycloalkyl group and an aryl group;
$R^2$ and $R^3$ are lower alkyl groups having from 1-6 carbon atoms, aryl groups, cycloalkyl and aralkyl; and
Q is $CO_2M+$ where M is an alkali or alkaline earth metal;
which comprises dispersing a compound represented by the formula:

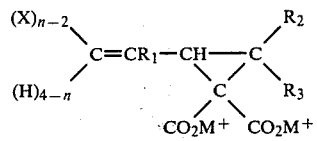

in an organic solvent inert to said compound thereby forming a dispersion, acidifying the dispersion with aqueous mineral acid, terminating acidification at a pH of 3-4 thereby forming a precipitate and then recovering the precipitate as product compound.

2. The process of claim 1 wherein $R^1$ is selected from the group consisting of hydrogen, methyl, ethyl, and phenyl.

3. The process of claim 2 wherein $R^2$ and $R^3$ are selected from the group consisting of hydrogen, methyl, ethyl, and phenyl.

4. The process of claim 3 wherein $R^1$ is hydrogen.

5. The process of claim 4 wherein $R^2$ and $R^3$ are methyl groups and n is 4.

6. The process of claim 5 wherein M+ is sodium or potassium.

* * * * *